United States Patent [19]

Wildon

[11] Patent Number: 4,972,833
[45] Date of Patent: Nov. 27, 1990

[54] EPICARDIAC PACING LEAD

[75] Inventor: Michael P. Wildon, Gooseberry Hill, Australia

[73] Assignee: WestMed Pty. Ltd., Osborne Park, Australia

[21] Appl. No.: 258,996

[22] PCT Filed: Jan. 22, 1987

[86] PCT No.: PCT/AU87/00015
§ 371 Date: Sep. 21, 1988
§ 102(e) Date: Sep. 21, 1988

[87] PCT Pub. No.: WO87/04355
PCT Pub. Date: Jul. 30, 1987

[30] Foreign Application Priority Data

Jan. 22, 1986 [AU] Australia .................. PH04301
Sep. 11, 1986 [AU] Australia .................. PH07951

[51] Int. Cl.$^5$ .............................. A61N 1/00
[52] U.S. Cl. ..................... 128/419 P; 128/784; 128/786
[58] Field of Search ............ 128/419 P, 784, 419 D, 128/786, 798

[56] References Cited

U.S. PATENT DOCUMENTS

| 3,719,190 | 3/1973 | Avery | 128/419 P |
|---|---|---|---|
| 4,112,952 | 9/1978 | Thomas et al. | 128/419 P |
| 4,317,458 | 3/1982 | Yokoyama | 128/784 |
| 4,341,226 | 7/1982 | Peters | 128/784 |
| 4,374,527 | 2/1983 | Iversen | 128/419 P |
| 4,530,368 | 7/1985 | Saulson et al. | 128/419 P |
| 4,567,900 | 2/1986 | Moore | 128/784 |
| 4,633,880 | 1/1987 | Osypka et al. | 128/419 P |

Primary Examiner—Francis Jaworski
Assistant Examiner—George Manuel
Attorney, Agent, or Firm—Harness, Dickey & Pierce

[57] ABSTRACT

An epicardiac pacing lead for ventricular or atrial pacing of the heat of a cardiac patient. The epicardiac pacing lead comprises a catheter housing two elongated electrical conductors one end of each of which is adapted for electrical connection to a source of electrical stimulation and the other end of which is connected to a respective stimulating electrode on the catheter. The section of the catheter adjacent the electrodes has a stiffness characteristic which allows the section to be bent manually and to maintain a configuration into which it has been bent while allowing the section to straighten automatically to follow the course of the catheter as it is withdrawn from the body of the patient. The end portion of the section adjacent the electrode is configured so as to provide a compression spring to facilitate location of the epicardiac pacing lead in position.

11 Claims, 2 Drawing Sheets

EPICARDIAC PACING LEAD

THIS INVENTION relates to an epicardiac pacing lead.

An epicardiac pacing lead is used to apply electrical stimulation to the heart of a cardiac patient from an external pacemaker. Electrical stimulation is normally used after sugical procedures on cardiac patients to correct arrythmic beating of the hear. The electrical stimulation may be applied to the atrium, to the ventricle or sequentially to the atrium and the ventricle of the heart.

The pacing lead has a stimulating electrode at one end and the other end is adapted for electrical connection to the pacemaker. The pacing electrode is implanted in the body of the patient, with the stimulating electrode in electrical contact with the heart. The pacing lead is affixed to the external surface of the heart and is threaded (at its other end) through the pericardium and the chest or abdominal wall of the patient for connection to the external pacemaker.

Epicardiac pacing leads which are currently in use are generally physically affixed to the heart either by suturing to epicardiac or other body tissue, or by means of a fixing device such as a prong or a screw-threaded element which is adapted to be embedded into the exterior surface of the heart. To remove the pacing lead from a patient, the pacing lead is manually pulled from the body of the patient. In doing this, the pacing lead is torn from the part of the body to which it has been physically attached, and this may result in tissue damage.

The present invention seeks to provide an epicardiac pacing lead which when implanted in the body of the patient is not physically affixed to the heart. In one form the invention resides in an epicardiac pacing lead comprising a catheter housing an elongated electrical conductor one end of which is adapted for electrical connection to a source of electrical stimulation and the other end of which is connected to a stimulating electrode on the catheter, characterised in that at least the section of the catheter adjacent the electrode has a stiffness characteristic which allows said section to be bent manually and to maintain a configuration into which it has been bent while allowing the section to straighten automatically to follow the course of the catheter as it is withdrawn from the body of the patient.

With this arrangement, said section of the catheter can be bent as desired (by a surgeon installing the pacing lead) into a position in which the electrode contacts the required part of the anatomy of a patient. The stiffness characteristic of said section is such that the section has sufficient rigidity to maintain the position in which it has been installed while having sufficient flexibility to straighten when being withdrawn from the body of the patient. The pacing lead is not required to be physically affixed to the heart either by suturing to epicardiac or other body tissue or by means of a fixing device such as a prone or screw threaded element. The lead is maintained in position because it is imbedded in the body of the patient.

The pacing lead may be used for ventricular pacing or atrial pacing.

Preferably the electrode is located at or near the inner end of the catheter, said inner end being that end which is implanted in the body of a patient when the catheter is in use.

Preferably, the end portion of said section adjacent the electrode is configured so as to provide a compression spring. With this arrangement, the compression spring can be compressed and in use inserted between the heart and the pericardium of the patient. When the compression spring returns to its extended position, it is retained between the heart and the pericardium with the electrode in electrical contact with the heart.

If a surgeon so desires, he or she may manually uncoil the spring formation or otherwise configure the catheter as required. Because of its stiffness characteristics, the catheter will retain the shape into which it has been bent by the surgeon.

To complete the electrical circuit between the body of the patient and the source of electrical stimulation, there is provided a second electrode for contacting the body of the patient, the second electrode being adapted for electrical connection to the electrical stimulation source. Preferably, the second electrode is mounted on the catheter at a location space from the stimulating elecrode and is connected to one end of a second elongated conductor which is housed in the catheter. The two electrical conductors within the catheter are electrically insulated from each other.

Preferably, each electrode is so shaped as to present relatively low physical resistance to oncoming body tissue as the catheter is withdrawn from a body of the patient. Each electrode may be mounted on, or in the form of a fixed spring. The fixed spring is so arranged as to extend generally along the catheter with the fixed end thereof being furthermost from the inner end of the catheter. In this way the fixed spring can collapse against the catheter when the latter is being withdrawn from the body of a patient.

The invention will be better understood by reference to the following description of one specific embodiment thereof as shown in the accompanying drawings in which.

Figure 1:
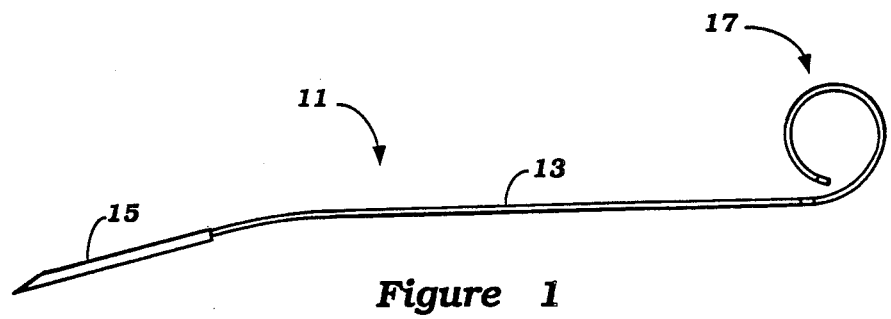
FIG. 1 is a view of an epicardiac pacing lead assembly according to the embodiment.
Figure 2:
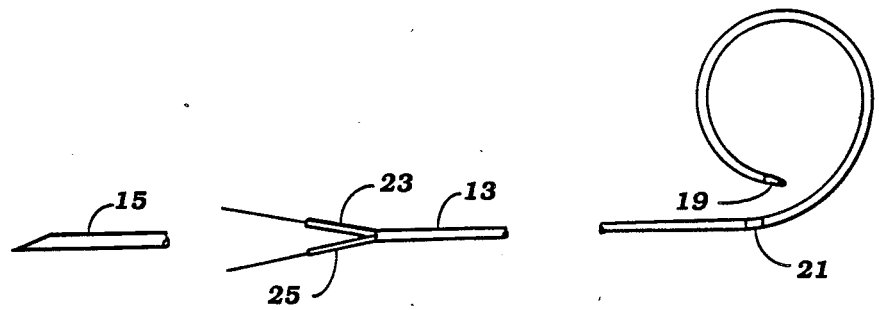
FIG. 2 is a fragmentary view showing each end of the pacing lead assembly of FIG. 1, with the threading needle removed from the outer end to reveal the terminal ends of the electrical conductors.

The embodiment shown in the drawings is directed to a pacing lead assembly 11 comprising a flexible hollow catheter 13 formed of biocompatible material such as polyethylene. The catheter 13 is adapted at one end to receive a detachable needle 15 to facilitate threading of the catheter through part of the body of a patient. The other end of the catheter is bent into the shape of a helical compression spring formation 17. The material from which the catheter is formed has a stiffness characteristic which allows it to be bent manually and to maintain a configuration into which it has been bent, while allowing any such bend, as well as the spring formation 17, to straighten automatically so as to follow the course of the catheter as it is being withdrawn from the body of a patient (as will be explained later).

Figure 3:
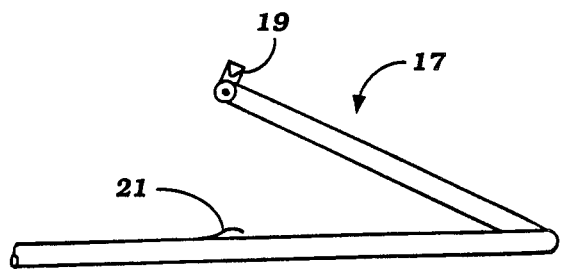
FIG. 3 is a detailed view of the inner end of the epicardiac pacing lead assembly.

On the spring formation 17 of the catheter there are mounted two electrodes, a first electrode 19 and a second electrode 21 either one of which may be a stimulating electrode. Each electrode is in the form of a fixed spring 22 (see FIG. 3) anchored at one point to the catheter so as to ordinarily protrude from the catheter, while being able to collapse into a position in which it lays against the catheter as the latter is being withdrawn from the body of a patient. In this way, the fixed spring when so collapsed provides relatively low physical resistance to oncoming body tissue as the catheter is withdrawn from the patient's body.

The first electrode 19 is connected to one end of a first elongated electrical conductor 23 in the form of a wire conductor. The second electrode 21 is connected to one end of a second elongated electrical conductor 25 also in the form of a wire conductor. The first and second elongated electrical conductors 23 and 25 are mounted in the hollow catheter and are electrically insulated from eachother and form the catheter. The other or terminal end of each of the first and second elongated electrical conductors extend beyond the end of the catheter 13 opposite the spring formation 17 and is adapted for electrical connection to a pacemaker (not shown). The terminal ends of the first and second conductors are covered by the needle 15 when the latter is fitted onto the catheter, as shown in FIG. 1 of the drawings.

The pacing lead assembly 11 is intended to be temporarily implanted in the body of a cardiac patient before the pericardium and chest wall are closed. The assembly may be located in position relative to the heart 24 (see FIG. 4) in one of two ways. One way of locating the assembly is to compress the spring formation 17 on the catheter and then locate the spring formation at an appropriate position in the zone between the exterior wall of the heart 24 and the pericardium. When the compressive force on the spring formation is released, the spring formation extends and one end thereof engages against a heart while the other end thereof engages against the pericardium thereby to clamp the spring formation in position. In this position, the first (stimulating) electrode 19 and the second electrode 21 are both in electrical contact with the heart. The catheter 13 is then fed through the pericardium and thorax of the patient with the aid of the needle 15. Following penetration of the chest wall of the patient, the needle is detached from the catheter so as to expose the terminal ends of the electrical conductors 23 and 25. The surgical procedure on the patient can then be completed as normal. In this arrangement, the cather is retained in position by the spring formation and by virtue of it being threaded through part of the body of the patient. The spring formation ensures that the two electrodes remain in electrical contact with the patient's heart.

Figure 4:
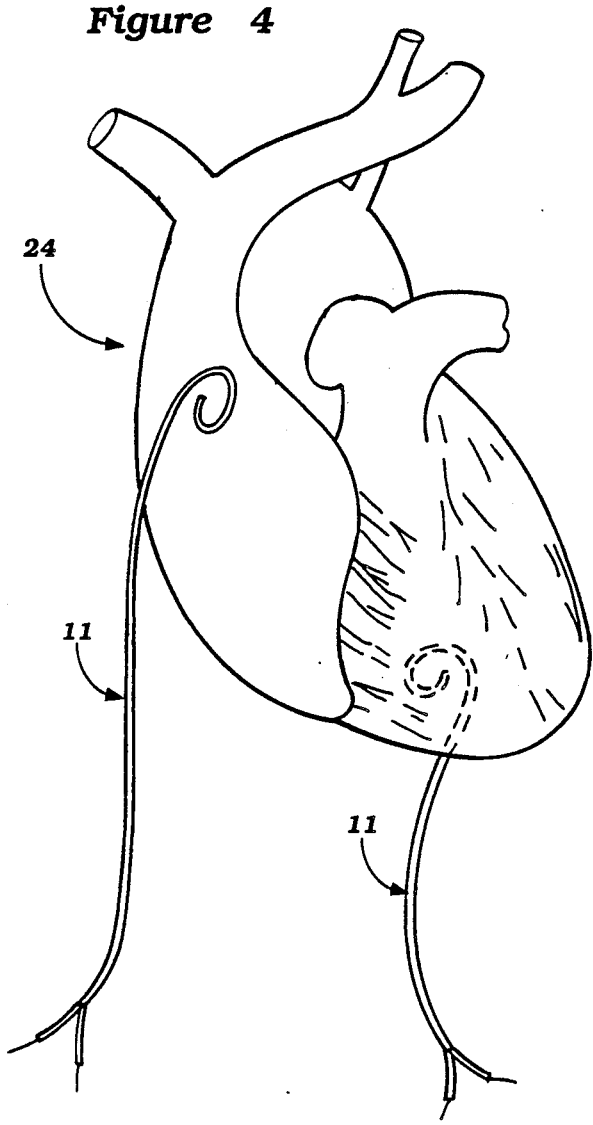
FIG. 4 is a schematic view showing two pacing lead assemblies implanted in a patient.

Another way in which the pacing lead assembly may be located in position relative to the heart will now be described. Rather than positioning the spring formation 17 between the heart and the pericardium, the surgeon may rely on the stiffness characteristics of the catheter to maintain the position of the catheter relative to the heart when the catheter is implanted in the body of the patient. With this procedure, the surgeon would feed the catheter through the pericardium and thorax of the patient with the aid of the needle 15, in a manner similar to that previously described. After the catheter has been implanted in the body of the patient, the surgeon manually deforms the inner end section of the catheter so as to position the two electrodes 19 and 21 into electrical contact with the heart. The electrodes remain in contact with the heart owing to the stiffness characteristics of the catheter and the fact that the catheter is imbedded in the body of the patient. FIG. 4 of the drawings shows two pacing lead assemblies in position, one for atrial pacing and the other for ventricular pacing.

Should the heart of the patient require electrical stimulation in the post-operative period, it is merely necessary to connect the pacemaker to the opposed terminal ends of the electrical conductors. When the patient has stabilised sufficiently to allow the epicardiac pacing lead assembly to be removed, it is simply pulled out through the chest wall. As the pacing lead assembly is pulled from the patient, the spring formation 17 and any bend manually formed in the catheter, straightens so as to facilitate withdrawal of the assembly. Because the assembly is not physically fixed to the heart, its removal can be achieved relatively easily and without tearing of, or other damage to, the tissue of the heart.

As the pacing lead assembly is withdrawn, the fixed springs collapse to a position against the catheter so as to not unduly restrict the withdrawal procedure or cause excessive tissue damage to the patient.

In addition to pacing an arrythemically beating heart, the pacing lead assembly can be used to stimulate the ventricle or atrium of the heart during the period of weaning of a patient off a heart-lung maching. In such application, the pacing lead assembly can be used to stimulate the heart to function on its own, and then be progressively moved to appropriate zones of the heart until the heart is beating without external assistance. Because the pacing lead assembly is not physically attached to the heart, it can be moved relatively easily between various zones of the heart during the surgical procedure. Although the invention has been described with reference to one specific embodiment, it should be appreciated that it is not limited thereto and that various alterations and modifications may be made without departing from the scope of the invention.

I claim:

1. An eqicardiac pacing lead comprising a catheter housing an elongated electrical conductor one end of which comprises an electrical connection to a source of electrical stimulation and the other end connected to a stimulating electrode on the catheter, for stimulating surface epicardial tissue characterized in that at least the section of the catheter adjacent said stimulating electrode has sufficient resilience to be bent manually upon insertion and for tending to return to its unbent configuration for resiliently maintaining said stimulating eleotrode in electrical contact with said surface epicardial tissue, said resilience being sufficient for said section to straighten automatically to follow the course of said catheter when it is withdrawn from the body of the patient.

2. An epicardiac pacing lead to claim 1 the electrode is located contiguous to one end of the catheter.

3. An epicardiac pacing lead according to claim 1 wherein said end portion of said section adjacent the electrode is configured for acting as a compression spring.

4. An epicardiac pacing lead according to claim 3 further comprising a second electrode for contacting the body of the patient, the second electrode being adapted for electrical connection to said electrical stimulation source.

5. An epicardiac pacing lead according to claim 3 further comprising a second electrode for contacting the body of the patient, the second electrode being adapted for electrical connection to said electrical stimulation source.

6. An epicardiac pacing lead according to claim 1 further comprising a second electrode carried by said catheter for contacting the body of the patient, the second electrode being adapted for electrical connection to said electrical simulation source.

7. An epicardiac pacing lead according to claim 6 wherein said second electrode is connected to one end of a second elongated conductor housed in the catheter.

8. An epicardiac pacing lead according to claim 6 wherein each electrode is so shaped as to present relatively low physical resistance to oncoming body tissue as the catheter is withdrawn from a body of the patient.

9. An epicardiac pacing lead according to claim 8 wherein each electrode is in the form of a fixed spring extending generally along the catheter with the fixed end thereof furthermost from the inner end of the catheter.

10. An epicardiac pacing lead according to claim 1 wherein the electrode is so shaped as to present relatively low physical resistance to oncoming body tissue as the catheter is withdrawn from a body of the patient.

11. An epicardiac pacing lead according to claim 10 wherein the electrode is includes a fixed spring extending generally along the catheter with the fixed and thereof futhermost from the inner end of the catheter.

* * * * *